US012471636B2

(12) United States Patent
Hall

(10) Patent No.: US 12,471,636 B2
(45) Date of Patent: Nov. 18, 2025

(54) COLD VAPE DEVICE

(71) Applicant: James Douglas Hall, Las Vegas, NV (US)

(72) Inventor: James Douglas Hall, Las Vegas, NV (US)

( * ) Notice: Subject to any disclaimer, the term of this patent is extended or adjusted under 35 U.S.C. 154(b) by 409 days.

(21) Appl. No.: 18/092,885

(22) Filed: Jan. 3, 2023

(65) Prior Publication Data

US 2024/0215647 A1 Jul. 4, 2024

(51) Int. Cl.
*A24F 40/485* (2020.01)
*A61M 15/06* (2006.01)

(52) U.S. Cl.
CPC ........... *A24F 40/485* (2020.01); *A61M 15/06* (2013.01)

(58) Field of Classification Search
None
See application file for complete search history.

(56) References Cited

U.S. PATENT DOCUMENTS

2005/0217311 A1* 10/2005 Armer ................. A47J 41/0077 62/530
2016/0044960 A1* 2/2016 O'Connor ................. A24F 1/00 131/200
2017/0055588 A1* 3/2017 Cameron .............. A61M 15/06
2020/0375262 A1* 12/2020 Aboabdo ................. H02K 1/02
2022/0338533 A1* 10/2022 Isozaki ...................... A24F 1/30
2023/0322470 A1* 10/2023 Gonzalez ........... B65D 81/3841 220/592.2
2024/0099306 A1* 3/2024 Yamaguchi ............. A24F 40/42

FOREIGN PATENT DOCUMENTS

KR 101250013 B1 4/2013

* cited by examiner

*Primary Examiner* — Philip Y Louie
*Assistant Examiner* — Jeffrey A. Buckman

(57) ABSTRACT

The invention pertains to a vaping like device comprising a mouthpiece with an outlet for inhaling, a shell comprising a housing, a module adapted to fit into the housing of the shell and adapted to be cooled to a temperature below 32° F., further comprising a circuit contacting the module and conveying outside air to the mouthpiece thus cooling the air inhaled through the mouthpiece.

17 Claims, 6 Drawing Sheets

COLD VAPE DEVICE

TECHNICAL FIELD

The invention pertains to the field of alternative smoking devices.

BACKGROUND OF THE INVENTION

Many smokers are looking for an alternative to smoking cigarettes, allowing them to enjoy their habit of smoking without the fear of addiction and health risks associated with smoking tobacco.

Such an alternative is, for instance, e-cigarettes or vapes, that work by heating a liquid and converting it into vapor which is inhaled. Depending on the kind of liquid, the vapor may or may not contain nicotine, but it any case it comprises chemicals that may also be harmful in the long run.

Therefore, the e-cigarette solution does not fulfill the objective of being a chemical free alternative to tobacco and evidence of it is that FDA considers e-cigarettes as tobacco even though they do not use tobacco.

SUMMARY OF THE INVENTION

The invention aims at proposing an alternative to smoking that may be free of any chemical while still providing a specific inhaling sensation.

To this end the invention pertains to a device comprising a mouthpiece with a hole for inhaling, a shell comprising a housing, a module adapted to fit into the housing of the shell and adapted to be cooled to a temperature below 32° F., further comprising a circuit contacting the module and conveying outside air to the mouthpiece thus cooling the outside air inhaled through the mouthpiece.

Therefore, the device provides a cool and refreshing inhaling sensation without adding any chemical to the inhaled air.

The device may be implemented according to the various embodiments exposed hereafter that are to be considered individually or according to any technically operable combination.

Advantageously, shell comprises an external double wall. Thus, the inside of the shell is insulated from outside hot air, and the module may be kept frozen for a longer time.

According to variants, the module is made of a material chosen among metal, glass and plastic.

According to an embodiment, the module is adapted to contain a fluid. The fluid may be water, or an eutectic gel.

Advantageously, the module adapted to contain a fluid is refillable.

Advantageously, the shell is made of a polymer loaded with microparticles made of a material selected among copper, silver and titanium oxide. Those microparticles act as antimicrobial agents and preclude the development of bacteria and microorganism in the shell, more particularly in the circuit.

According to an embodiment, the circuit conveying the inhaled air is formed in the shell. The circuit may be a helical circuit turning around the module, or, can be a labyrinth type circuit.

According to another embodiment, the circuit conveying the inhaled air is inside the module.

Whatever the embodiment, the length of the circuit is preferably equal or more than 8 feet. Such a length enhances thermal exchanges with the module.

According to a specific embodiment the device further comprises an electrical circuit adapted to supply energy to a Peltier cell comprising a cold plate and a warm plate and adapted to cool the module when it is energized. This embodiment allows to cool the module inside the device when the electrical circuit is plugged to an energy source.

To this end, according to an exemplary embodiment, the device further comprises a battery compartment and a battery adapted to provide power to the electrical circuit.

Advantageously, the device further comprises a micro-fan powered by the electrical circuit, and air blown by the micro-fan is directed to the warm plate of the Peltier cell.

Advantageously, the device further comprises a cartridge holder and a flavor cartridge holder in an air stream towards the mouthpiece and adapted to release a flavor in the air stream.

Advantageously, air blown by the micro-fan is directed to the flavor cartridge.

BRIEF DESCRIPTION OF DRAWINGS

The invention is hereby disclosed in its preferred embodiments in no way limiting, and in reference to FIGS. 1 to 6 in which.

DETAILED DESCRIPTION OF THE INVENTION

Figure 1:
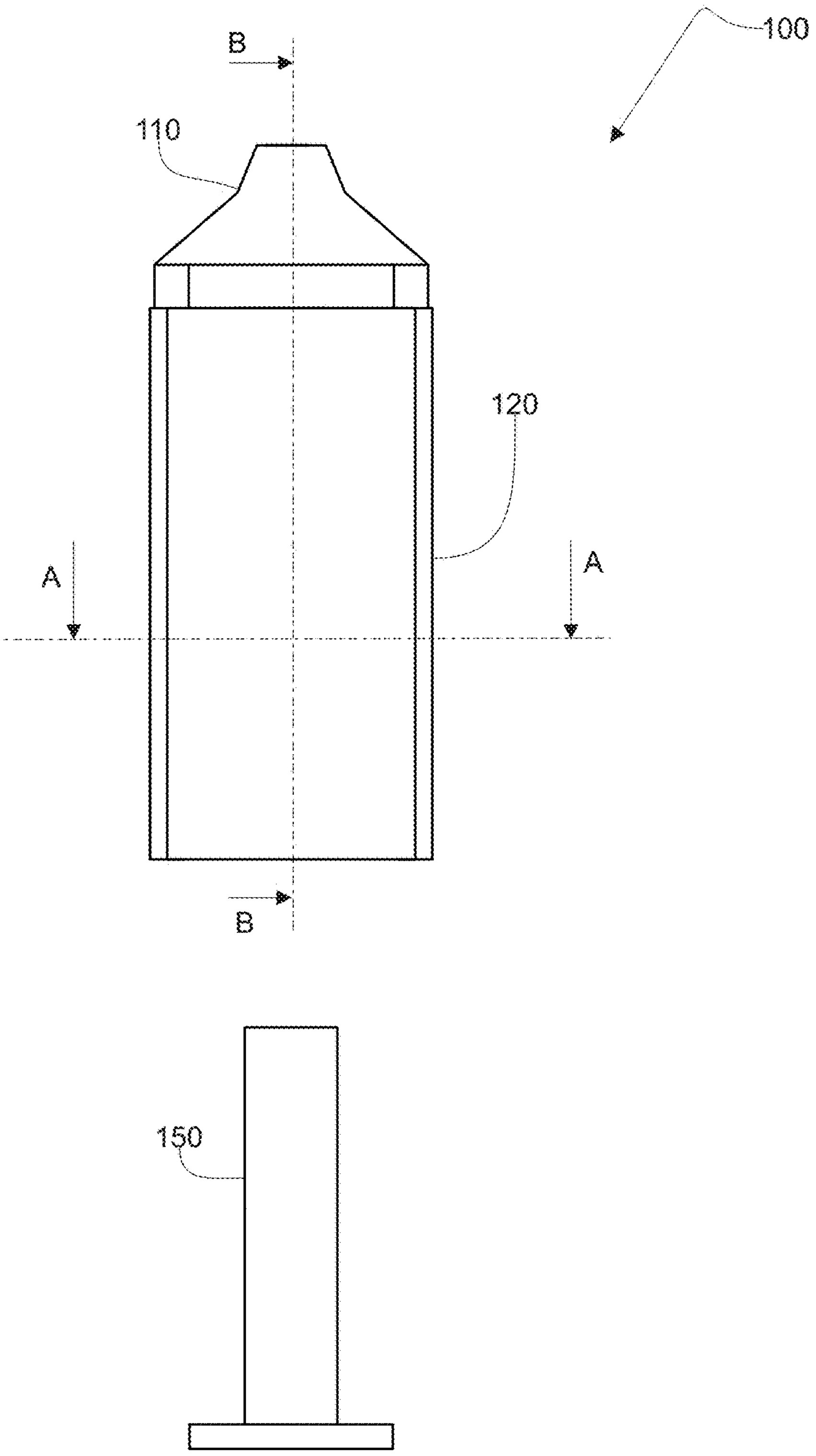
FIG. 1 shows a front exploded view of an embodiment of the device of the invention

FIG. 1, according to a first embodiment the device of the invention (100) looks like a conventional vaping device and comprises a mouthpiece (110) by which a user may inhale air, and a shell (120) adapted to house a module (150). The module (150) is e.g. clipped into the shell.

According to variants, the module is a solid piece or a hollow piece adapted to contain a fluid, The module is made of metal, glass or plastic, advantageously coated by a layer of highly thermally conductive material such as copper, silver or gold.

The fluid may be water, like tap water, in such a case the module may be refillable, or the fluid may be an eutectic gel made of a mixture of water with an eutectic agent and a viscosifier. In the latter, the fluid is preferably sealed into the module.

According to various embodiments the eutectic agent is a salt, e.g. sodium chloride or a polymer like methylcellulose sodium, without these examples being limiting.

The viscosifier may be a paraffin, a fatty acid or a sugar alcohol, without these examples being limiting.

The shell and the mouthpiece may be made integral, however, according to a preferred embodiment the mouthpiece is disposable and may be changed for hygienic purpose, In the latter embodiment the mouthpiece may be made of food grade silicone.

The shell Is made of plastic, preferably a thermoplastic in order to allow mass production by injection molding. Advantageously, the plastic of the shell is loaded with microparticles known for their antimicrobial properties such as copper, silver or titanium oxide.

For the device to operate, the module shall be cooled to a temperature below 32° F. and be introduced into the shell.

The module may be cooled by simply placing it in a freezer or, according to a specific embodiment described under, the device may comprise its own cooling means.

Figure 2:
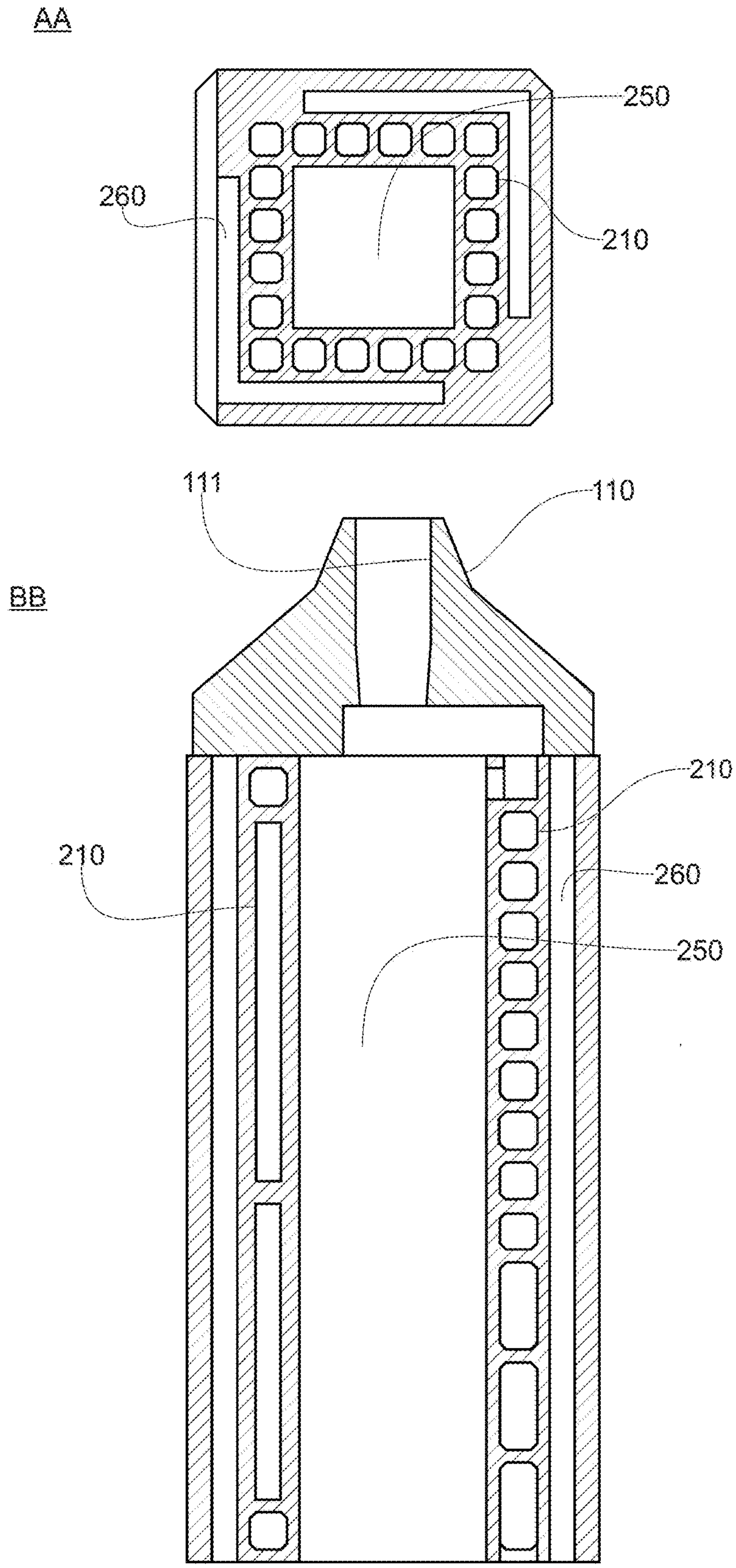
FIG. 2 shows the device of FIG. 1 in cross sections AA and BB defined in FIG. 1

FIG. 2, according to this exemplary embodiment, the module is pushed in, from the bottom of the shell, in a module housing (250) in the middle of the shell. The shell comprises a labyrinth type circuit (210), forming a main inhaled air circuit, conveying inhaled outside air and contacting the nodule for thermal exchange between the inhaled air and the module.

When the user inhales air through the mouthpiece (110), air is sucked in at the bottom of the shell, i.e. at the end of the shell opposite the mouthpiece, and enters a conduit extending in a labyrinth type circuit (210) where the air is cooled as it travels up to the mouthpiece through the conduit contacting the cold module.

In this exemplary embodiment the conduit is folded and refolded to make a labyrinth path with a total developed length of about 8 feet. In an alternative embodiment the conduit is wrapped around the module housing (250), as a helicoid, also providing a total developed length of about 8 feet.

A hollow volume (260) is provided between the outside wall of the shell and the conduit following the labyrinth type circuit (210), thus making a double wall and enhancing thermal insulation between the outside wall and the conduit. Alternatively, this hollow volume may be filled with a thermally insulating material.

Figure 3:
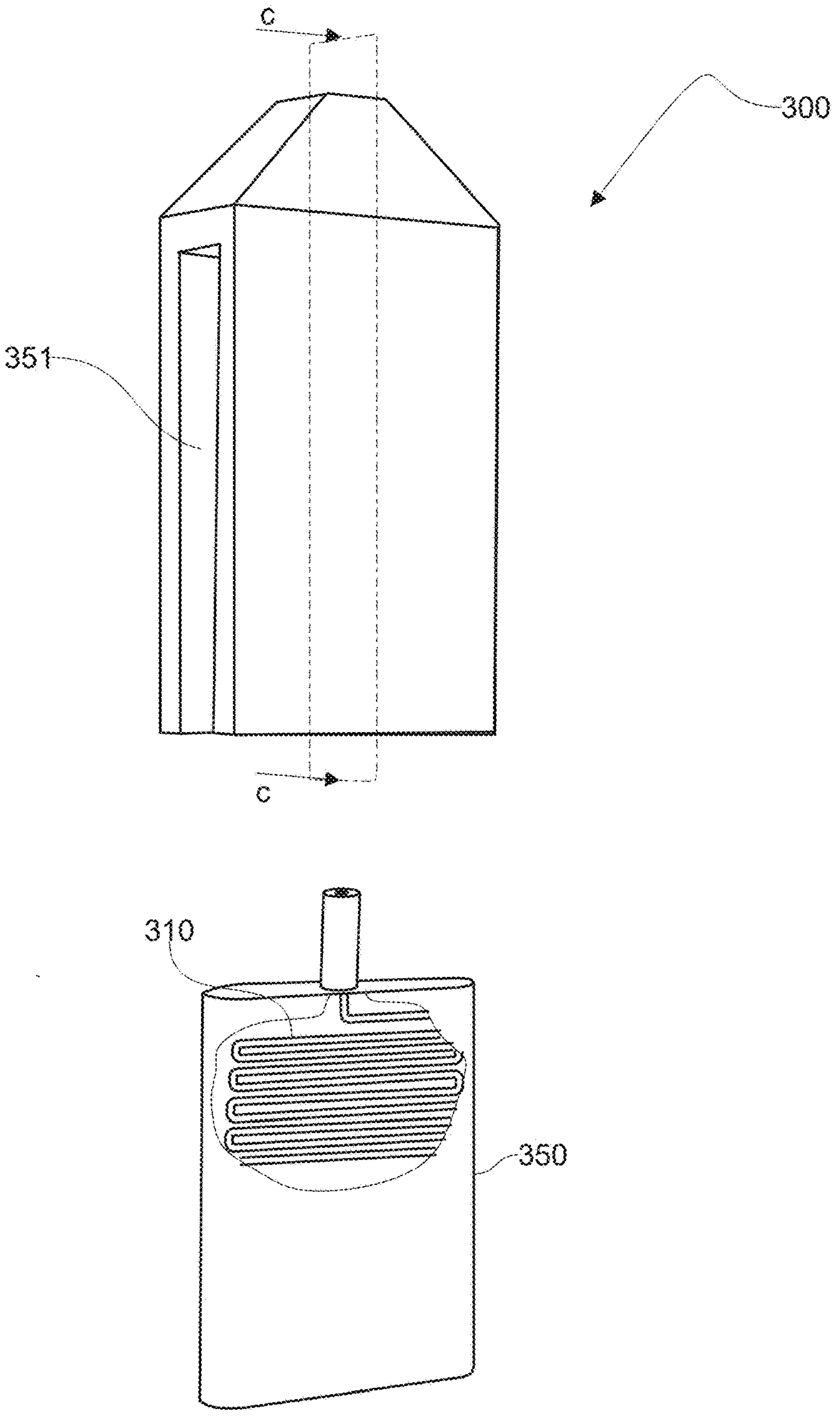
FIG. 3 represents in an exploded perspective view another exemplary embodiment of the device of the invention

FIG. 3, according to another embodiment of the device (300), the shell comprises a slot (351) allowing a module (350) with an overall quadrangular shape to be slid in the slot. The shell further comprises clipping means (not shown) to hold the module in place once inserted into the slot.

According to this embodiment the shell is made of plastic, e.g. of a biosourced polymer, and the module (350) is made of a rigid material like metal or glass, thus providing stiffness to the assembly when inserted into the slot (351) of the shell.

In this embodiment the module is sealed and contains an eutectic gel.

Advantageously the main inhaled air circuit (310) conveying inhaled air is inside the module directly contacting the eutectic gel.

Figure 4:
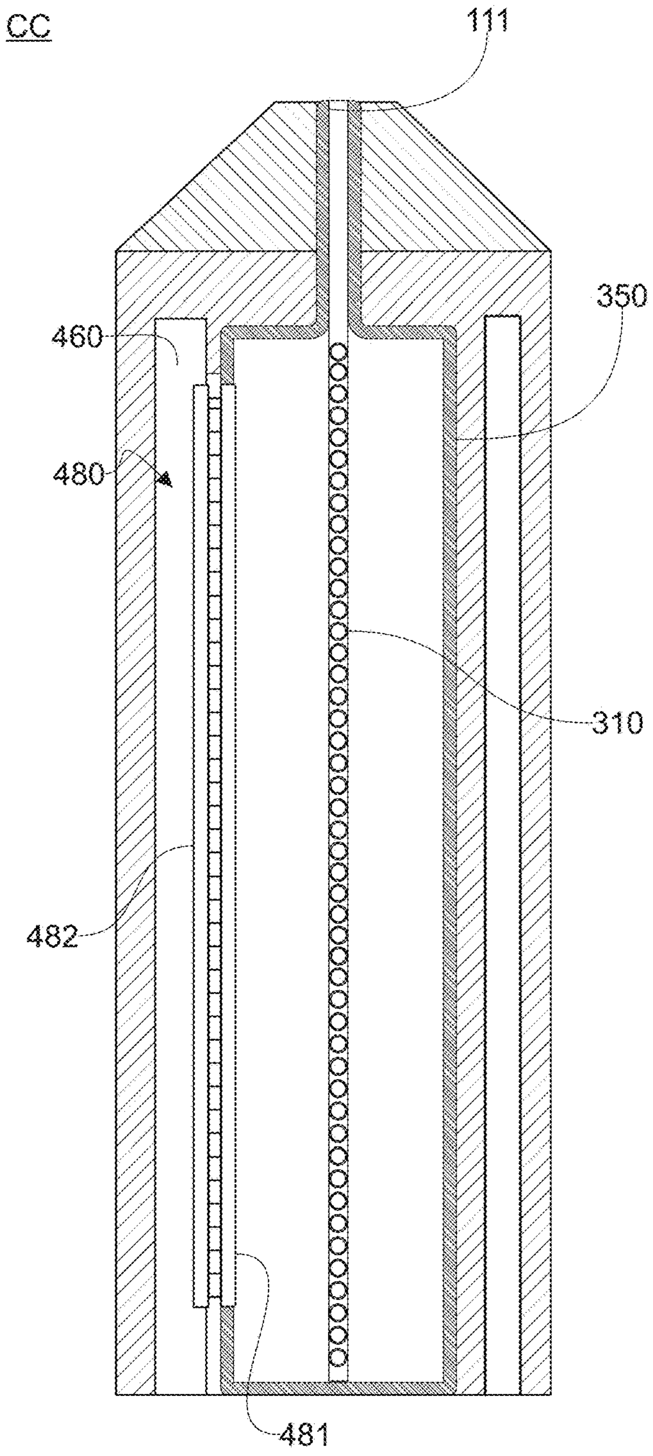
FIG. 4 shows an improvement of the embodiment of FIG. 3 according to a CC cross section defined in FIG. 3

FIG. 4, according to an improved embodiment the device further comprises a Peltier cell (480) used to cool the module.

According to variants the cold face of the Peltier cell (481) may be set inside the module, directly contacting the eutectic gel, or may be set outside the module, contacting one face of said module (not shown).

According to this embodiment the device comprises means to energize the Peltier cell, e.g. an electrical circuit connected to a micro-USB connector and/or to a battery, thus allowing the user to freeze the module without requiring the module to be placed in a freezer.

Whatever the variant, the warm face (482) of the Peltier cell is preferably but not exclusively, set into the hollow space (460) in between the double walls of the shell, so that it is thermally insulated from both the module and the from the hand of the user.

Figure 5:
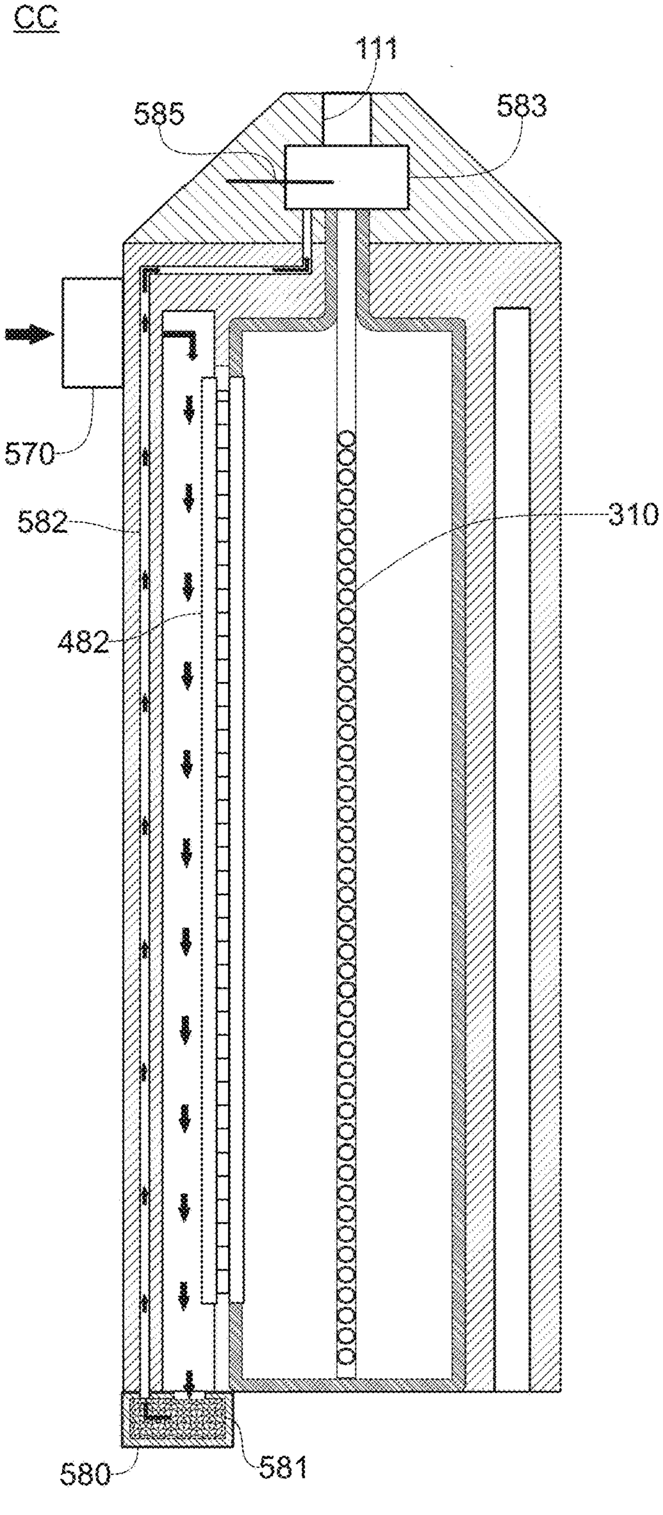
FIG. 5 is still another embodiment shown according to the CC cross section.

FIG. 5, advantageously, a micro-fan (570) is powered by the same means as the Peltier cell and blows air on the warm face (482) of the Peltier cell, thus favoring heat evacuation.

According to a specific embodiment (not shown), the warm plate of the Peltier cell may be connected to a heat sink.

FIG. 5, according to still another embodiment, the device may comprise a cartridge holder (580) adapted to contain a flavoring cartridge (581) for releasing a flavor into a flavored air stream that is part of the air inhaled by the user when using the device.

According to variants, this favored air stream may be conveyed by the main inhaled air circuit and be cooled by contacting the module, alternatively or in addition, the flavored air stream may be conveyed by a secondary circuit (582) close to the mouthpiece.

In the latter, a mixing box (583) may be set upstream of the mouthpiece outlet (111).

The flavoring cartridge comprises a substrate in which a flavoring agent is confined and which is adapted to release a flavor when submitted to a stream of air, preferably warm air.

As a nonlimiting example, the substrate may be a non-woven fibrous material and the flavoring agent may be an essential oil impregnating the substrate.

In another nonlimiting example, the flavoring agent, for instance an essential oil, may be encapsulated in polymer beads and the substrate is a small permeable cloth bag containing said beads.

The micro-fan may be used to blow air into the secondary circuit. This allows to blow a controlled stream of warmer air, whether outside ambient air or air heated by contacting the warm face (482) of the Peltier cell, thus favoring the release of the flavor.

By controlling the quantity of air injected by the micro-fan in the secondary circuit (582), with regard to the quantity of air inhaled through the main circuit (310), e.g. though a switch, the user may control the temperature of the inhaled air as well as the intensity of the flavoring.

In another embodiment the device may comprise a temperature sensor (585), e.g. a thermocouple, in the mixing box (583) connected to an electronic circuit thus providing a temperature information, said electronic circuit piloting the micro-fan so as to control the inhaled air temperature.

Figure 6:
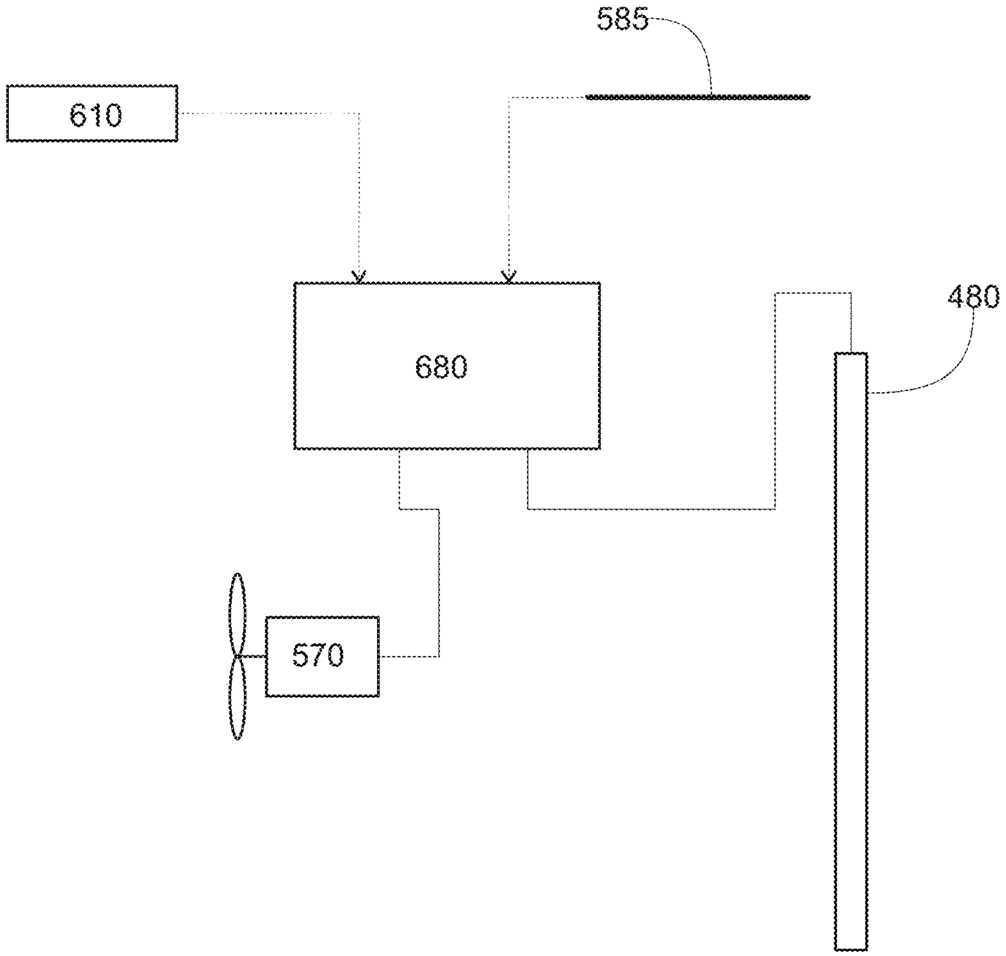
FIG. 6 is a diagrammatic representation of an embodiment comprising an automatic controller of the temperature of the inhaled air.

FIG. 6 according to this embodiment, the device comprises a user interface (610), which can be as simple as a switch with a 3 colors LED, allowing him to select the coldness of the inhaled air like, as a nonlimiting example: “fresh”, “cold” and “iced”. This selection is transmitted as a setpoint to the electronic circuit (680) and compared with the temperature measured by the temperature sensor (585).

Accordingly, the electronic circuit will pilot the electric current delivered to the Peltier cell (480) and the spinning speed of the micro-fan (570) or alternatively when and how long the micro-fan is triggered in order to get the temperature measured by the temperature sensor (585) closer to the setpoint.

The above description of the exemplary embodiments shows that the invention achieves its aim in providing an alternative to smoking and conventional vaping, the device providing when in use a refreshing air stream devoid of chemicals.

The vaping device of the invention may also be used to help preventing heat strokes in hot climates.

It may also be used with or without specific cartridges in rehabilitation assistance as an alternative to drugs.

The invention claimed is:

1. A device comprising a mouthpiece comprising an outlet for inhaling air, a shell comprising a central opening surrounded by internal walls forming a module housing, a module adapted to fit and be slid into the module housing, the module contacting the internal walls, the module being configured to be cooled to a temperature below 32° F., further comprising a main inhaled air circuit consisting in a conduit with a developed length of at least 8 feet, formed in a thickness of walls of the shell, comprised between outside walls of the shell and the internal walls, contacting the module over the developed length and conveying an air stream consisting of outside air free of added chemical to the outlet, thus cooling the air stream.

2. The device of claim 1, wherein the shell comprises a hollow volume comprised between the conduit and the outside walls, configured to make a double wall for thermal insulation between the outside walls and the main inhaled air circuit.

3. The device of claim 1, wherein the module is made of a material chosen among metal, glass and plastic.

4. The device of claim 3, wherein the module is configured to contain a fluid.

5. The device of claim 4, wherein the fluid is water.

6. The device of claim 4, wherein the fluid is a eutectic gel.

7. The device of claim 3, wherein the module is refillable.

8. The device of claim 1, wherein the shell is made of a polymer loaded with microparticles made of a material selected among copper, silver and titanium oxide.

9. The device of claim 1 or claim 8, wherein the shell is made of a bio-sourced polymer.

10. The device of claim 1, wherein the conduit of the main inhaled air circuit is in shape of a helicoid wrapped around the module housing.

11. The device of claim 1, wherein the conduit of the main inhaled air circuit forms a labyrinth circuit.

12. The device of claim 1, further comprising a Peltier cell and an electrical circuit for supplying energy to the Peltier cell, wherein the Peltier cell comprises a cold face and a warm face, the cold face being set in a location selected among inside the module and contacting a face of the module.

13. The device of claim 12, further comprising a battery compartment and a battery to supply energy to the electrical circuit.

14. The device of claim 13, further comprising a micro-fan powered by the electrical circuit.

15. The device of claim 14, wherein an air blown by the micro-fan is directed to the warm face of the Peltier cell.

16. The device of claim 1, comprising a secondary circuit, a cartridge holder and a flavor cartridge, the secondary circuit conveying a flavored air stream into a mixing box upstream of the outlet.

17. The device of claim 16, further comprising a micro-fan powered by an electrical circuit, the micro-fan blowing air contacting the flavor cartridge in the secondary circuit.

* * * * *